United States Patent [19]
Joshi et al.

[11] Patent Number: 5,785,688
[45] Date of Patent: Jul. 28, 1998

[54] FLUID DELIVERY APPARATUS AND METHOD

[75] Inventors: Ashok V. Joshi, Salt Lake City; James O. Davis, Sandy; Truman Wold, Salt Lake City; Giorgio di Palma, Draper, all of Utah

[73] Assignee: Ceramatec, Inc., Salt Lake City, Utah

[21] Appl. No.: 646,069

[22] Filed: May 7, 1996

[51] Int. Cl.$^6$ ................................................ A61M 37/00
[52] U.S. Cl. .......................... 604/141; 604/132; 604/145; 604/153
[58] Field of Search ................................... 604/131, 132, 604/140, 141, 145–147, 153, 410, 416

[56] References Cited

U.S. PATENT DOCUMENTS

| | | |
|---|---|---|
| 187,031 | 2/1877 | McMorries . |
| 2,168,437 | 8/1939 | Buercklin . |
| 2,545,017 | 3/1951 | Billingsley . |
| 2,832,339 | 4/1958 | Sarnoff et al. . |
| 2,971,509 | 2/1961 | Cohen . |
| 3,115,280 | 12/1963 | Battista . |
| 3,433,224 | 3/1969 | Black . |
| 3,468,308 | 9/1969 | Bierman . |
| 3,506,005 | 4/1970 | Gilio et al. . |
| 3,640,277 | 2/1972 | Adelberg . |
| 3,894,538 | 7/1975 | Richter . |
| 3,951,147 | 4/1976 | Tucker et al. . |
| 4,059,110 | 11/1977 | Wuthrich et al. . |
| 4,140,122 | 2/1979 | Kuhl et al. . |
| 4,201,207 | 5/1980 | Buckles et al. . |
| 4,203,441 | 5/1980 | Theeuwes . |
| 4,265,241 | 5/1981 | Portner et al. . |
| 4,265,874 | 5/1981 | Bonsen et al. . |
| 4,351,335 | 9/1982 | Whitney et al. . |
| 4,360,019 | 11/1982 | Portner et al. . |

(List continued on next page.)

OTHER PUBLICATIONS

"Appendix C Infusion Devices", *Appendix C*, pp. 933–938.
Baxter Healthcare Corporation/Infusion Systems Division, Product Information Sheet (1 page).
Baxter, "I.V. Therapy That Goes To Work", *The Remington Report*, Feb./Mar. 1995, 2 pages.
Baxter, "Stratofuse PCA™ Portable, programmable infusion system", 2 pages.
"Dependable Drug Delivery AmbuFlow An Innovative Mini Infusion System for Ambulatory Patients", 6 pages.
Disetronic Medical Systems,"The Disentronic Infusor", 4 pages.
"FDA gives green light to testing needleless system", *The Associated Press* (1 page).
Flock et al., "The Venisect Er: Yag Laser—Laser Mediated Skin Perforation and Laser Assisted Transdermal Drug Delivery", *University of Arkansas Medical Sciences*, 7 pages.
Irwin et al. "Evaluation Of A Disposable Patient–Controlled Analgesia Device In Children", *British Journal of Anaesthesia*, 1992, 68:411–413.

(List continued on next page.)

*Primary Examiner*—Sam Rimell
*Assistant Examiner*—Robert V. Racunas
*Attorney, Agent, or Firm*—Dick and Harris

[57] ABSTRACT

An apparatus (120) useful for, among other things, subcutaneous drug delivery includes a housing (124), a fluid reservoir (154) disposed within the housing for storing the fluid, a pump or pressurized chamber for pressurizing a driving gas and exerting a force on the fluid reservoir to expel the fluid reservoir's contents, and a needle (150) or absorbent pad fluidically communicating with the reservoir. The apparatus may further include a pump activation mechanism such as a button and an electrical circuit such that pushing the button activates a circuit and connects a battery (138) to a pump (126), and a pump control mechanism such as electrical circuitry to control the voltage gradient to a pump to control fluid delivery.

21 Claims, 6 Drawing Sheets

U.S. PATENT DOCUMENTS

| | | |
|---|---|---|
| 4,395,259 | 7/1983 | Prestele et al. . |
| 4,447,232 | 5/1984 | Sealfon et al. . |
| 4,457,752 | 7/1984 | Vadasz . |
| 4,474,575 | 10/1984 | Eckenhoff et al. . |
| 4,525,164 | 6/1985 | Loeb et al. . |
| 4,552,561 | 11/1985 | Eckenhoff et al. . |
| 4,561,856 | 12/1985 | Cochran . |
| 4,596,575 | 6/1986 | Rosenberg et al. . |
| 4,626,244 | 12/1986 | Reinicke . |
| 4,634,431 | 1/1987 | Whitney et al. . |
| 4,636,197 | 1/1987 | Chu . |
| 4,640,445 | 2/1987 | Yamada . |
| 4,652,261 | 3/1987 | Mech et al. . |
| 4,673,392 | 6/1987 | Keime . |
| 4,687,423 | 8/1987 | Maget et al. . |
| 4,715,850 | 12/1987 | Tran . |
| 4,734,092 | 3/1988 | Millerd . |
| 4,744,786 | 5/1988 | Hooven . |
| 4,767,402 | 8/1988 | Kost et al. . |
| 4,775,361 | 10/1988 | Jacques et al. . |
| 4,781,689 | 11/1988 | Sealfon et al. . |
| 4,850,971 | 7/1989 | Colvin . |
| 4,886,499 | 12/1989 | Cirelli et al. ............... 604/131 |
| 4,898,582 | 2/1990 | Faste . |
| 4,966,585 | 10/1990 | Gangemi . |
| 4,969,873 | 11/1990 | Steinbach et al. . |
| 4,969,874 | 11/1990 | Michel et al. . |
| 5,041,094 | 8/1991 | Perego et al. . |
| 5,045,601 | 9/1991 | Capelli et al. ............... 525/327.1 |
| 5,062,834 | 11/1991 | Gross et al. . |
| 5,090,963 | 2/1992 | Gross et al. ............... 604/132 |
| 5,135,498 | 8/1992 | Kam et al. . |
| 5,135,499 | 8/1992 | Tafani et al. . |
| 5,167,625 | 12/1992 | Jacobsen et al. . |
| 5,190,558 | 3/1993 | Ito . |
| 5,242,565 | 9/1993 | Winsel . |
| 5,290,240 | 3/1994 | Horres, Jr. . |
| 5,318,540 | 6/1994 | Athayde et al. ............... 604/141 |
| 5,354,264 | 10/1994 | Bae et al. . |
| 5,368,571 | 11/1994 | Horres, Jr. ............... 604/131 |
| 5,383,851 | 1/1995 | McKinnon et al. . |
| 5,405,614 | 4/1995 | D'Angelo et al. . |
| 5,415,629 | 5/1995 | Henley . |
| 5,423,803 | 6/1995 | Tankovich et al. . |
| 5,427,870 | 6/1995 | Joshi et al. ............... 429/27 |
| 5,441,490 | 8/1995 | Svedman . |
| 5,454,922 | 10/1995 | Joshi et al. . |
| 5,456,679 | 10/1995 | Balaban et al. ............... 604/143 |
| 5,464,386 | 11/1995 | Hofmann . |
| 5,492,534 | 2/1996 | Athayde et al. ............... 604/141 |
| 5,578,005 | 11/1996 | Sancoff et al. ............... 604/141 |

OTHER PUBLICATIONS

Mackey et al. "Laboratory Evaluation of the Baxter Patient–Controlled Analgesia Infusion System: A Disposable Patient–Controlled Analgesia Device", *Anesth. Analg.*, 1993, 77:117–120.

New IV Products & Services, vol. 17, No. 6, Nov./Dec. 1994, pp. 311–312.

O'Keefe et al., "Patient–controlled analgesia using miniature electrochemically driven infusion pump", *British Journal of Anaesthesia*, 1994, 73:843–846.

Robinson et al., "Electronic and disposable patient–controlled analgesia systems", *Anaesthesia*, 1992, vol. 47, pp. 161–163.

Rowbotham et al., "A disposable device for patient–controlled analgesia with fentanyl", *Anaesthesia*, 1989, vol. 44, pp. 922–924.

Smart Dose™ Infusion System, River Medical, Inc., 2 pages.

10th Annual Buyer's Guide to Pumps & Controllers, *The Pharmacy Practice News*, Jul. 1994, pp. 21–26.

Theratron, "Infusion System For Intravenous Application", Mar. 15, 1995 (with English translation).

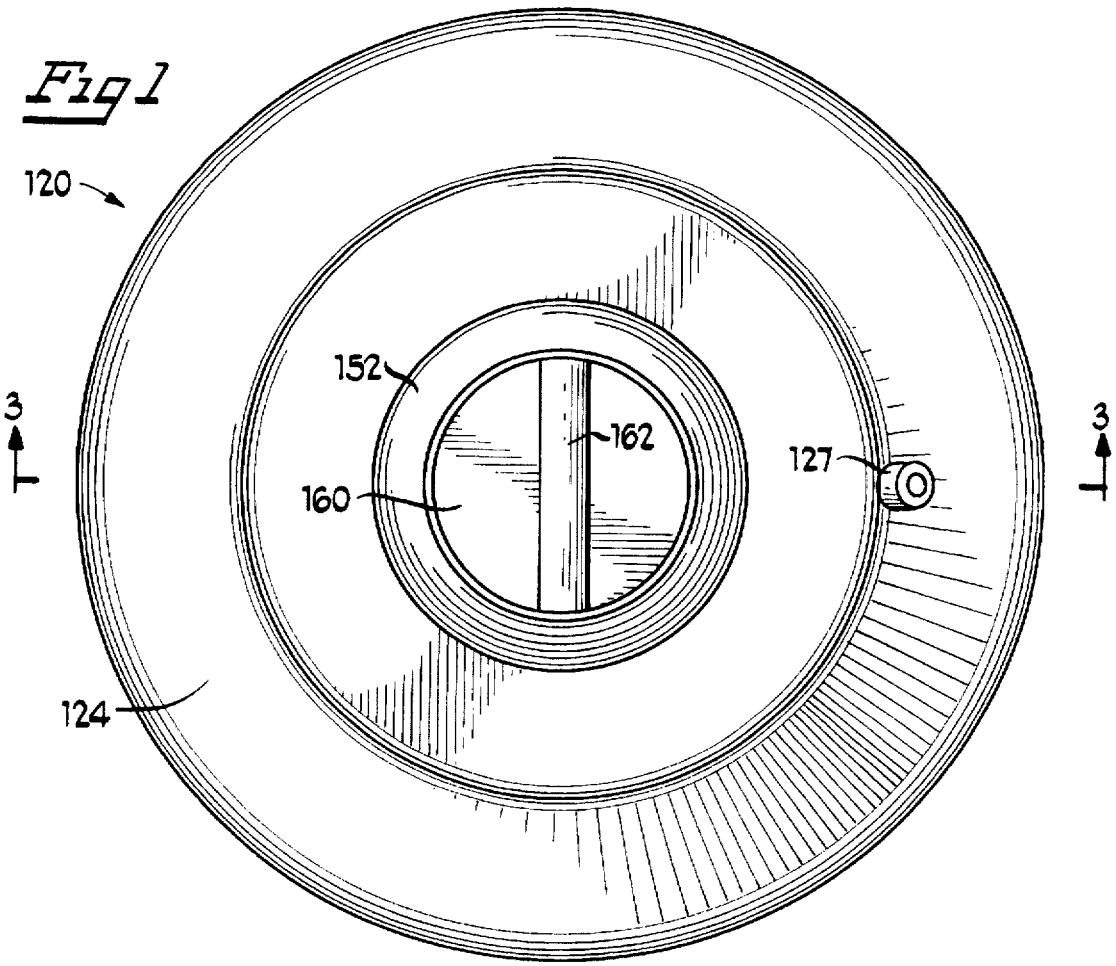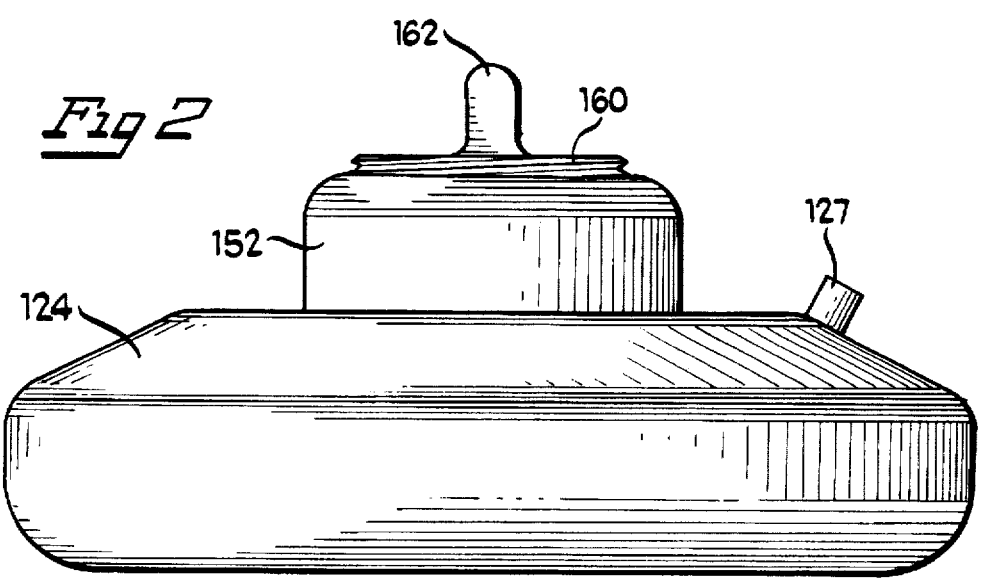

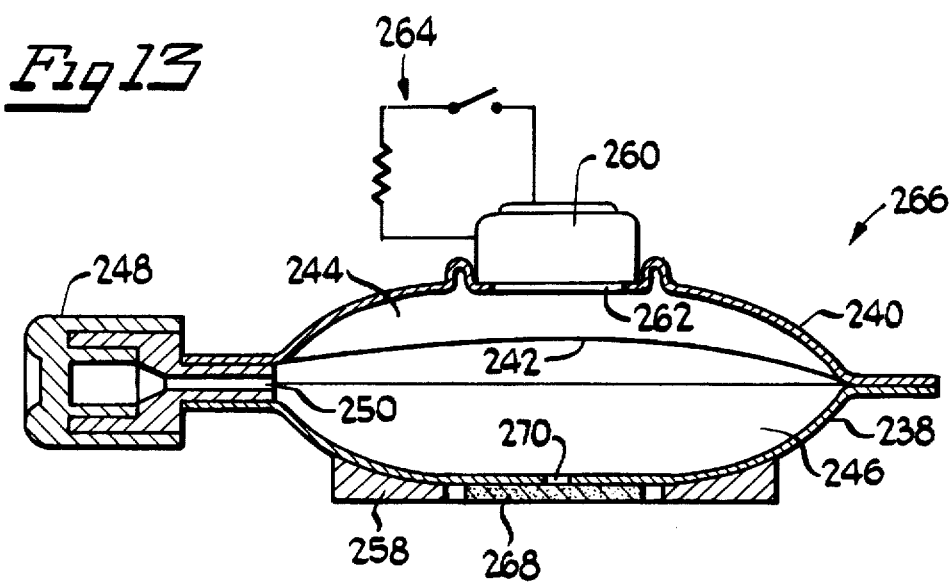
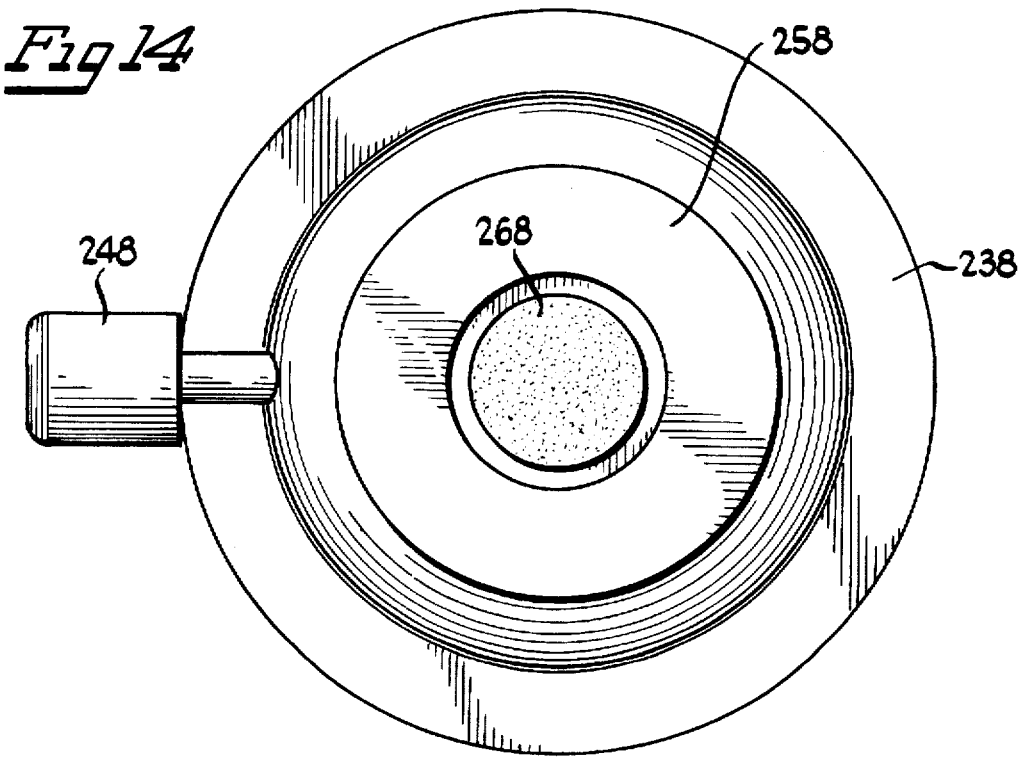

FLUID DELIVERY APPARATUS AND METHOD

TECHNICAL FIELD

The invention relates generally to methods and associated apparatus for controllably delivering fluids, and specifically to methods and associated apparatus for the slow infusion of a fluid, such as a liquid containing a biologically active substance.

BACKGROUND

In many medical situations it is necessary or desirable to administer small amounts of medicines and other pharmaceutical fluids to a patient's body over a relatively long period of time. For example, heparin is administered to a patient in need thereof by an intravenous "drip" procedure. Other medicines which may be administered over long periods of time include antiarrhythmics, streptokinase, "TPA", vitamins, hormones, and corticosteriods. Other medicines that can benefit from prolonged delivery periods include analgesics, anesthetics, antibiotics, cytostatics, and cytotoxics.

These medicines may be administered intermittently by bolus injection or continuously by gravity dispensers. Bolus injections may, however, imperfectly match the patient's actual requirements and subject the patient to larger dosages of drugs than required as well as frequent needle insertion. Continuous drug delivery through gravity dispensers may limit the patient's lifestyle by tethering him or her to the familiar intravenous drip apparatus. Furthermore, the dispensing rate is not always constant.

Portable units to deliver medicines have been developed that employ mechanical pumps, pressurized gas or the property of an elastic material to return to its original shape. The mechanical pumps use electrical or clockwork motors. The pressurized devices use elastic, inflated balloons or the vapor pressure of a volatile propellant. These devices suffer from many of the drawbacks of the gravity dispensers. Although portable, they generally remain bulky. The mechanical units have moving parts subject to wear and are relatively expensive. They also may have difficulty dispensing small volumes of liquid accurately.

Gas generating devices have been developed that are both portable and accurate for dispensing small volumes. These gas generating methods include osmotic pumps, electrolytic cells, Galvanic cells, and oxygen pumps.

An osmotic pump involves imbibing water or another driving fluid. The ump consists of three chambers: a salt chamber, a water chamber, and a drug chamber. The salt and water chambers are separated by a semipermeable membrane. This membrane is permeable to water but impermeable to salt. The drug chamber is separated from the other two by a flexible diaphragm. Water imbibes osmotically into the salt chamber creating an osmotic pressure which, in turn, exerts a force on the diaphragm thus expelling the drug.

An electrolytic cell comprises a pair of electrodes suspended in an electrolyte. When voltage is applied to the electrodes, the electrolyte gives off a gas which exerts a force on a diaphragm or piston thus expelling the drug.

A Galvanic cell is essentially a metal/electrolyte cell where hydrogen gas is created by reaction of metal with electrolyte thus completing the contact between metal and cathode. The anode and cathode are connected through a resistor. The resistor regulates the current passed through the cell which directly regulates the production of gas.

An oxygen pump transports oxygen from one side of a membrane to the other. Electrodes are placed on opposite surfaces of an electrolytic membrane. Then a voltage gradient is established across the electrolytic membrane. Oxygen is ionized at the first electrode and passes through the membrane where it is reconverted into oxygen at the second electrode. This oxygen can be captured to provide pumping action through the inflation of a bag.

Portable drug delivery systems have been described. For example, U.S. Pat. No. 4,552,561 to Eckenhoff et al. (Nov. 12, 1985) discloses a rigid, tapered housing that is affixed to the wearer by an annular adhesive overlay. Enclosed within the housing is a chamber for the medicament, an imbibing pump, and a traditional needle. One drawback of such a system is that a rigid housing may not easily conform to the contours of the user's body. Another problem is that the flow rate of an osmotic pump varies with temperature. A change in body or external temperature could have the undesirable effect of changing the medicament flow. In addition, in order to vary the medicament flow, it may be necessary to provide numerous osmotic pumps with differing outputs, or hydrogels with different osmotic properties, or various impermeable membranes to partially preclude the osmotic pump. These limitations make it difficult for the patient to use and control such devices. Osmotic pumps also require charging (the time required for liquid to diffuse through the semipermeable membrane and begin dissolving the osmagent at steady state) which delays the delivery of the medicament and which limits their suitability for instantaneous or emergency use.

U.S. Pat. No. 4,734,092 to Millerd (Mar. 29, 1988) discloses a flexible housing that is attached to the subject by an adhesive surface incorporated on the housing. Enclosed in the housing is a pump module, a cannula, and a fluid conduit passageway in the form of a spirally wrapped tube. The pump transports atmospheric oxygen into the tube. Such pumping creates a pressure which drives the medicament through the cannula. An oil slug separates the medicament and oxygen. The device is actuated by removing a peel tab and rotating the pump so that the output of the pump aligns with the input of the spiraled tube. The flow can be controlled by varying the current to the pump with a potentiometer. One drawback of such a device is the use of added components for a filtering system of hydrophobic and hydrophilic membranes to keep oil and oxygen from being administered to the patient. Thus, the hydrophobic membrane keeps the medicament in the device while allowing the oxygen to escape. The hydrophilic membrane allows medicament to pass into the body while obstructing oxygen. The hydrophilic membrane is of limited porosity so that it also impedes oil. Another disadvantage of this device is the protrusion of the cannula while in the storage or non-use stage. This exposes the device to possible damage and contamination. Also, a protruding needle does little to re-assure a traumatized or needle-phobic patient. An additional drawback is the difficulty in manufacturing a device with a spiral wrapped tube.

Another development in drug delivery systems is the transdermal patch. The patch is attached to the skin by an adhesive surface. Medicine then passes through the patch and the skin. A drawback of transdermal drug delivery technology is that certain molecules are very difficult to administer in effective doses. In addition, control of the drug administration may be limited.

DISCLOSURE OF THE INVENTION

The invention relates to an apparatus ideally suited for the slow infusion of a fluid, such as a biologically active material, into a subject's (e.g. a mammal's) body. The apparatus is inexpensive to manufacture, easy to use, and reliable. In one embodiment, the apparatus is self-contained, inconspicuous and concealable, innocuous in appearance, and capable of being rapidly implemented.

In general, the apparatus includes a housing, a fluid reservoir (or multiple reservoirs) disposed within the housing for storing the fluid to be delivered, a pump to create a driving gas which exerts a force on the fluid reservoir to expel the fluid reservoir's contents, and means for fluid delivery (e.g. a cannula, needle or pad),for example, cannula being in fluid communication with the fluid reservoir. The apparatus may further include a pump activation mechanism such as a button and electrical circuit wherein, by pushing the button, one activates the circuit, electrically connecting a power source (e.g. a battery) to the pump. The apparatus may still further include a pump control mechanism (e.g. an electrical circuit that controls the voltage gradient to the pump) so that delivery of the fluid is controlled.

A different housing for use with an apparatus according to the invention includes a displaceable diaphragm dividing the housing into two chambers wherein the first chamber contains the fluid to be delivered, and the second chamber contains a driving gas. The driving gas chamber may include a pressure relief valve or burst (or rupture) disc. A pump may be included to pressurize the driving gas, thus exerting a force on the first chamber to expel the fluid to be delivered, and a cannula or needle in fluid communication with the fluid to be delivered from the first chamber.

Alternatively, the apparatus may include a generally inexpandable housing, a deformable fluid reservoir disposed within the housing, a pressurized driving gas source to exert a force on the fluid reservoir to expel the fluid thus contained, and an associated cannula for controllably and constantly delivering the fluid.

The apparatus may include adhesive or an adhesive layer positioned on the housing's surface for adhering the apparatus to the subject's body. In such an embodiment, a protective backing can be removed and the apparatus then applied to the subject's body. Thus, the apparatus is readily adapted to emergency situations. The apparatus can further utilize either a separate layer of anesthetic and/or antiseptic generally disposed on the surface of the housing in the vicinity of the cannula such that the subject's body is desensitized where the cannula will be inserted, or may include such medicaments with the adhesive layer.

BRIEF DESCRIPTION OF THE FIGURES

In the drawings, which depict preferred embodiments of the invention and in which like reference numerals refer to like parts in different views:

FIG. 1 is a top plan view of a slow infusion subcutaneous fluid delivery apparatus embodying features of the present invention.

FIG. 2 is a side view of the device of FIG. 1.

FIG. 13 is an enlarged section view of an embodiment of the invention.

FIG. 14 is an enlarged bottom view of the embodiment of the preceding figure.

DETAILED DESCRIPTION OF THE INVENTION

Figure 3:
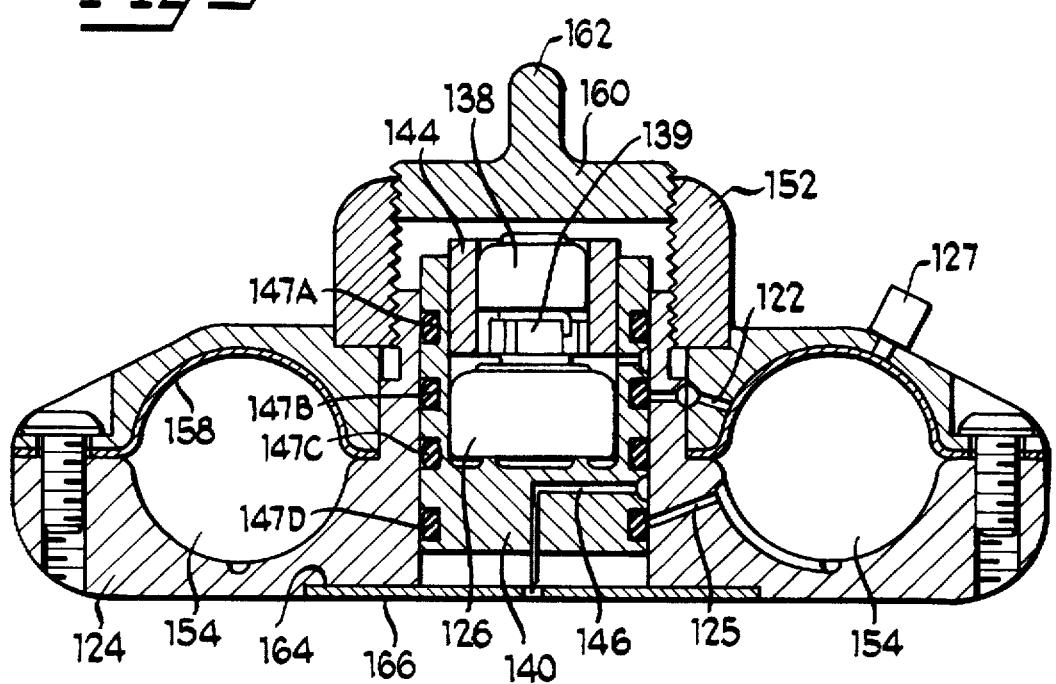
FIG. 3 is an enlarged cross-sectional view of the apparatus of FIG. 1 with the apparatus being shown in section taken substantially along line 3—3 of FIG. 1 before actuation of the device.

As depicted in FIGS. 1–4, in a preferred embodiment, an apparatus according to the invention, generally 120, includes a bladder or compressible reservoir 154,156 containing a fluid (e.g. a liquid) containing a biologically active substance, such as a medication. This reservoir 154,156 in turn, is associated with (e.g. contained in) a generally inexpandable housing 124.

The apparatus 120 includes a displaceable membrane 158 disposed within the housing such that the reservoir 154,156 is divided into two chambers; the first chamber 154 containing the fluid to be delivered and the second chamber 156 containing the driving gas. Pressure accumulated in the second chamber 156 exerts a force on the first chamber 154 so that the fluid to be delivered is expelled from the first chamber 154 and the flexible membrane 158 (being impermeable to the driving gas) prevents contamination of one fluid with another.

A needle, cannula 150 or other delivery means (e.g. a sponge-like pad) is in fluid communication with the reservoir so that when the reservoir's contents are expelled, they will flow through the delivery means. The length of a needle will typically be chosen to be slightly longer than the thickness of the tissue (e.g. skin) to be pierced.

Figure 5:
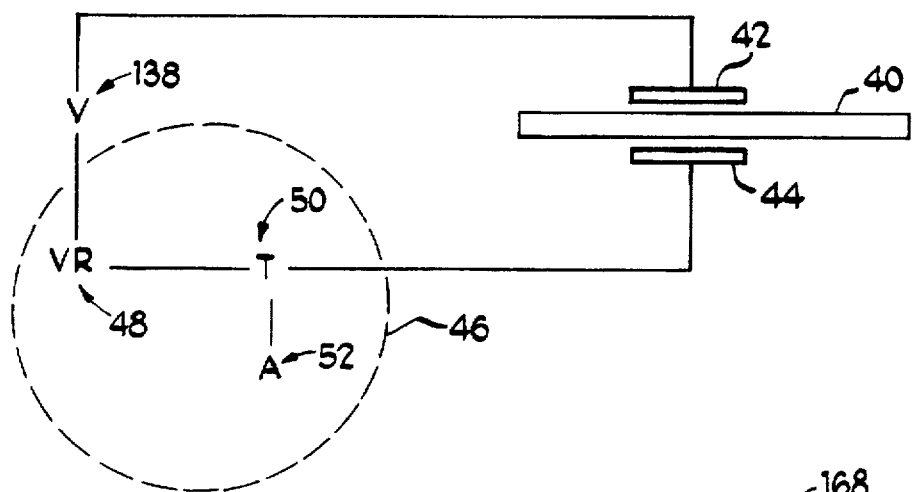
FIG. 5 schematically depicts circuitry useful in the practice of the invention.

The device has a pump 126 (e.g. a Galvanic cell or metal electrolyte cell), which is preferably, a hydrogen or oxygen pump. The pump may be a gas releasing electrochemical cell such as those disclosed in U.S. Pat. Nos. 5,427,870 (Jun. 27, 1995) and 5,454,922 (Oct. 3, 1995) to Joshi et al., the contents of the entirety of both of which are incorporated by this reference. As shown in FIG. 5, a battery 138 or other energy source may be used to establish a voltage gradient across the permeable membrane 40. Between the battery 138 and the pump 126 is a resistor holder 139. One pole of the battery is connected to an electrode 42. The other pole of the battery is connected to another electrode 44 on the other surface of the membrane. Atmospheric oxygen is ionized at electrode 42. The ions then pass through membrane 40 and are reconverted into oxygen at electrode 44.

The pump may be controlled by an electrical circuit 46 (within dashed lines of FIG. 5). The electrical circuit 46 can be connected between one of the connections between the battery and the cell. The circuit may contain a variable resistor 48 to vary the voltage gradient across the membrane. In addition, a timer 50 and/or alarm 52 could be incorporated into the circuitry to control the delivery of the fluid. In one embodiment, the electronic circuit is controlled by means of a microprocessor, controlling delivery of the fluid for, for example, diurnal or metabolic (e.g. mealtime) variations.

The pump may include its own housing (which may be part of the apparatus housing), an electrolytic membrane disposed in this housing having first and second surfaces, an opening for exposing the first surface to atmospheric oxygen or other source of driving gas (e.g. oxygen or hydrogen), a first material-pervious electrode disposed on the first membrane surface and a second material-pervious electrode disposed on the second membrane surface, and an electrical power source disposed within or on the housing for establishing a voltage gradient across the electrolytic membrane such that the oxygen is ionized at the first electrode, transporting the ions through the electrolytic membrane, wherein the ions evolve into oxygen molecules at the second electrode to become the driving gas. The pump may be an oxygen pump for transferring atmospheric oxygen into the housing and the driving gas comprises oxygen. The pump may alternatively be an electrolytic cell comprising a pair of electrodes suspended in an electrolyte and a voltage source such that when voltage is applied to the electrodes a gas is formed in the electrolyte which exerts a force that expels the liquid, or the pump may be a Galvanic cell.

A separate, replaceable pump module which contains a supply of fluid to be delivered may be used. In such a device, the activation mechanism may be a) temporary (e.g. active only when the module is pressed down, b) semi-permanent (e.g. similar to a retractable ball point pen mechanism), or c) permanent (e.g. once engaged, the device can only be stopped by removing the entire device or the module).

The pump control mechanism may further include a timer 50 such that the flow of the delivery fluid and the flow of the fluid reservoir contents can be timed, or an alarm so that an alarm is sounded on the occurrence of an event such as the passage of time, excessive pressure, excessive volume, etc.

In an alternative embodiment, the pump is replaced by a pressurized housing. This housing is also divided into a first chamber and a second chamber by a displaceable membrane (e.g. a flexible plastic piece). The first chamber contains the fluid to be delivered (e.g. insulin) and the second chamber contains the driving gas (e.g. oxygen or FREON™). The driving gas is pressurized at body temperatures so that it exerts a force on the membrane and expels the fluid to be delivered through the delivery means (e.g. an injection needle).

The fluid flow may be controlled. For example, a rotatable restrictor may be incorporated into the housing. A conduit is contained within the rotatable member. When rotated, one end of the conduit becomes aligned with an output from the fluid reservoir or first chamber while the other end of the conduit becomes aligned with an input of the cannula. When thus aligned, the fluid to be delivered flows through the cannula and is thus delivered. Continued rotation of the rotational member causes the conduit to become misaligned thus slowing or stopping the flow. Such a mechanism may be used to regulate the fluid flow subcutaneously as well as to control the flow of driving gas from the pump into the housing.

In one embodiment, the association between the housing and the reservoir is such that if a pressurized gas were introduced into the housing, the pressure thus created would exert a force on the exterior surface of the compressible reservoir. Also contained in such an apparatus is a pump or cell. The pump transfers a driving gas into the inexpandable housing. This driving gas pressurizes the interior of the housing, thus exerting a force on the exterior of the reservoir. The interior of the reservoir is in fluid communication with a tube or conduit extending away from the reservoir, preferably to the place where the contents of the reservoir are to be delivered. When pressure is exerted on the exterior of the reservoir, the contents of the reservoir are driven into one end of the tube and out the other end for delivery.

The tube or conduit may be comprised of various (e.g. two) distinct sections, and may be used to control the flow of material from the reservoir for delivery. The second section of conduit is contained in a solid rotatable member housed by the housing. By rotating the rotatable member, one end of the first section of the conduit may be brought in partial or complete alignment with a corresponding end of the second section of the conduit. By so doing, the contents of the fluid reservoir may be driven to a needle, cannula or absorbent pad for delivery of the fluid reservoir's contents. By controlling the amount of alignment between the two sections of the conduit, the amount of fluid delivered to the cannula can be controlled.

When used for the parenteral administration of a biologically active substance, the second section of the conduit and the lumen of the cannula may be filled with a biologically compatible fluid (e.g. water or normal saline). As used herein, the term "biologically active substance" means all types of medical and biological fluid used in the treatment of humans and animals including but not limited to peptides (such as insulin), analgesics, antiarrhythmics, steroids, hormones, nicotine, vitamins, anti-migraine medicine, anti-coagulants, local anesthetics, vaccines, allergens, muscle relaxants, etc. It should also be recognized that the apparatus is suited for the delivery of fluid into mammals, plants, fish, reptiles, and birds.

The needle or cannula is preferably contained within the housing during storage or when otherwise not in use, and, as described herein in more detail, extends or protrudes through the housing when actuated for use. When activated, the mechanism extends the cannula through the housing for insertion into the subject's body upon activation. When finished, the mechanism may then retract the cannula into the housing. This helps to keep the cannula sterilized and also protects against accidental damage. It also has the added benefit of concealing the cannula from people who are traumatized or needle-phobic. In one embodiment (not shown) the cannula activation mechanism is like a retractable pen mechanism; the cannula is extended and retracted by pushing a button associated with the device.

The surface of the housing that abuts or is in contact with the skin may be coated with an adhesive layer for attaching the apparatus to the skin. A protective backing (not shown) may be used to cover the adhesive layer during non-use. The adhesive layer preferably contains anesthetic, antiseptic, or a mixture thereof. When attached to the skin, the anesthetic desensitizes it, while the antiseptic disinfects it.

Alternatively, a chamber of anesthetic or antiseptic (generally disposed between the housing and the skin of the user) may be used to anesthetize or disinfect the local area (not shown).

In the event a transdermal route of administration is selected, transdermal permeation enhancers may be utilized to improve the transport of physiologically active agents through the skin or other membranes of an animal (e.g. a mammal). Transdermal permeation enhancers are disclosed in U.S. Pat. Nos. 3,989,816, 4,316,893, and others to Rajadhyaksha (e.g. lactams such as AZON™), U.S. Pat. No. 4,755,535 to Minaskanian, U.S. Pat. No. 4,699,777 to Zupon et al., U.S. Pat. No. 4,820,711 to Pearlman, U.S. Pat. No. 4,557,934 to Cooper, and U.S. Pat. No. 5,296,222 to Peterson et al., the contents of all of which are hereby incorporated by this reference.

When a device according to the invention uses a transdermal pad to deliver the liquid for administration to a patient, the skin may be pre-treated. A lancet, laser, keratolytic (e.g. salicylic acid solution), sand paper or other means may be used to disturb the stratum corneum to increase permeation before application of the device according to the invention.

The materials used in constructing the components of the invention will be selected to be compatible with the various reactants and products.

The present invention overcomes the shortcomings of transdermal technology by allowing larger molecular substances to be administered in a controlled manner to a patient's body. The present invention also overcomes the shortcomings of the "pump systems" by allowing for an inexpensive, reliable, and portable drug infusion device.

The invention is further explained by the following illustrative

EXAMPLES

Example I

A device is built as depicted in FIGS. 1–4. The apparatus, generally 120, has a housing 124 comprised of various hereinafter described parts. The housing 124 contains two annular fluid reservoirs defined by two compartments 154, 156. The first compartment 154 contains the fluid (e.g. an analgesic) to be delivered. The second compartment is to receive a driving gas (e.g. oxygen) produced by an electrochemical gas generating cell or pump 126. In the depicted device, the second compartment contains a pressure relief valve 127 for use in case of over pressure. In the depicted embodiment, the pump 126 is powered by a battery 138. The compartments 154, 156 are separated by an insoluble, water impermeable, polymeric (e.g. polyethylene) flexible membrane 158. The sum of the volumes of the two compartments 154, 156 remains generally constant.

In the device of FIGS. 1–4, the first compartment 154 is fluidically associated with a discharge conduit 125. Conversely, the second compartment 156 is associated with an input conduit 122 for receiving driving gas produced by the electrochemical gas generating cell 126.

The cell 126 and the battery 138 are associated with one another as a module 140 by means of a container 142 made of a conductive metal. Included within the depicted module 140 are the cell 126, the battery 138, an electrical insulating member 144, and a conduit 146 for fluidically connecting a needle 150 or other delivery means with the discharge conduit 125. The module 140 is sealed from the atmosphere by 0-rings (e.g. five or six) contained within compartments 147A-D aligned in the interior of the device 120.

One part of the housing 124 is a threaded female member 152. This threaded female member 152 cooperatively interacts with an electrically conductive, threaded male member 160. This threaded male member 160 has a knob 162. When the knob 162 is turned clockwise, it moves the threaded male member 160 down the threaded female member 152 driving the module 140 into a position wherein the conduit 146 fluidically interacts with the discharge conduit 125, and any gas produced by the cell 126 is in fluid communication with the input conduit 122 (compare FIG. 3 with FIG. 4). Upon actuation, the threaded male member 160 comes into physical contact with the battery 138. This completes the electrical circuit between the battery and metal container 142, and gas generation starts.

Figure 4:
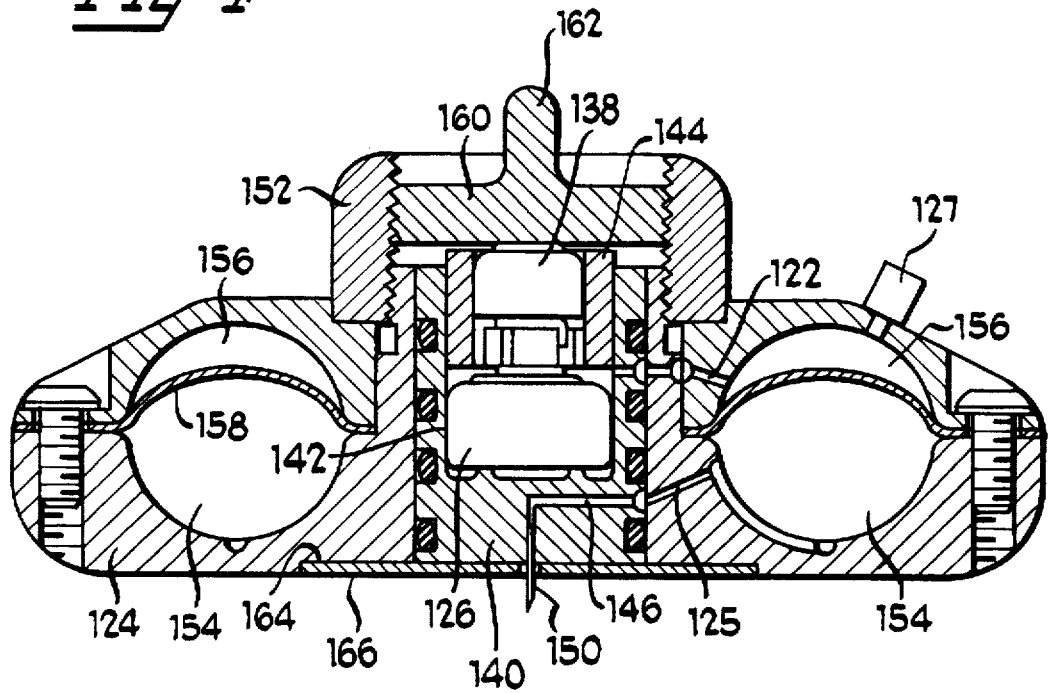
FIG. 4 is another enlarged cross-sectional view of the apparatus of FIG. 1 after actuation.

As depicted in FIGS. 3 & 4, the housing 124 also includes an indentation 164 for receipt of a layer 166 for containing compounds such as adhesives, antiseptics, and local anesthetics. Adhesives for use with skin are preferably hypoallergenic substances such as silicone adhesive formulations known to those of skill in the art. The layer 166 includes compounds such as antiseptics (e.g. ethanol) and a local anesthetics (e.g. benzocaine). In one embodiment (not shown) the needle 150, upon actuation of the male threaded member 160 actually pierces the layer 166 containing local anesthetic and antiseptic.

Example II

A cover off the adhesive layer 166 is peeled of the device of EXAMPLE I. The device has a potent anti-coagulating compound (e.g. TPA from Genentech) contained within the reservoir 154 and normal saline contained within the conduit 146 associated with the needle 150 and within the lumen of the needle 150. The device is adhered to a subject's skin. The antiseptic and local anesthetic associated with the adhesive layer act to disinfect and anesthetize the skin. The knob 162 is turned clockwise in the housing 152, thereby completing an electrical connection between the battery 138 and the cell 126, while, at the same time, aligning the input 122 and discharge conduits 125 with the corresponding members 146 of the module 140. The module's movement downward within the device also causes the end of the needle 150 to protrude through the level of the adhesive layer 166 and into and through the skin a length sufficient to administer a compound subcutaneously.

Upon electrification, the cell 126 begins generating oxygen. This oxygen gas builds up within the module 140 and passes out into the input conduit 122 and, therethrough, to the second compartment 156. The second compartment 156 fills with oxygen (FIG. 4). Since the sum of the volumes of the two compartments 154, 156 remains constant, the membrane 158 constricts about the first compartment 154, expelling fluid through the discharge conduit 125 and into the conduit 146 associated with the needle 150. Normal saline (or a similar fluid), previously placed in the conduit 146 is thus dispensed from the needle 150, followed by fluid previously contained within the first compartment 154. Since the flow of oxygen into the second compartment 156 is constant, a constant flow of fluid is dispensed from the device 120 and maintained.

Example III

Figure 6:
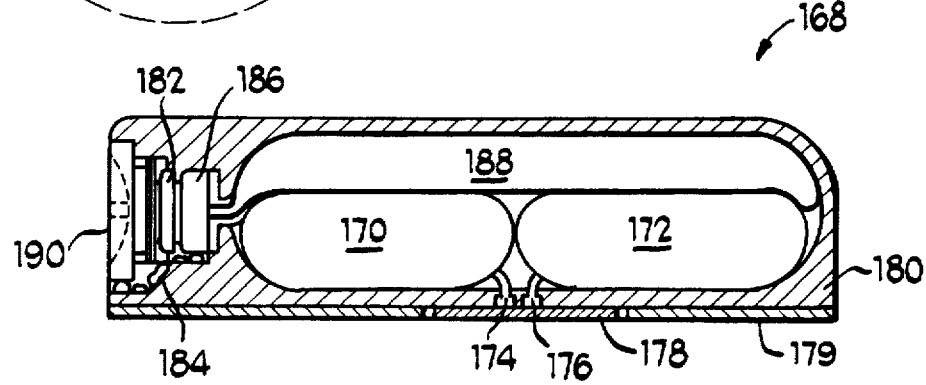
FIG. 6 is an enlarged cross-sectional view of another embodiment of the invention, wherein the apparatus has two reservoirs, and is designed for transdermal drug delivery.
Figure 7:
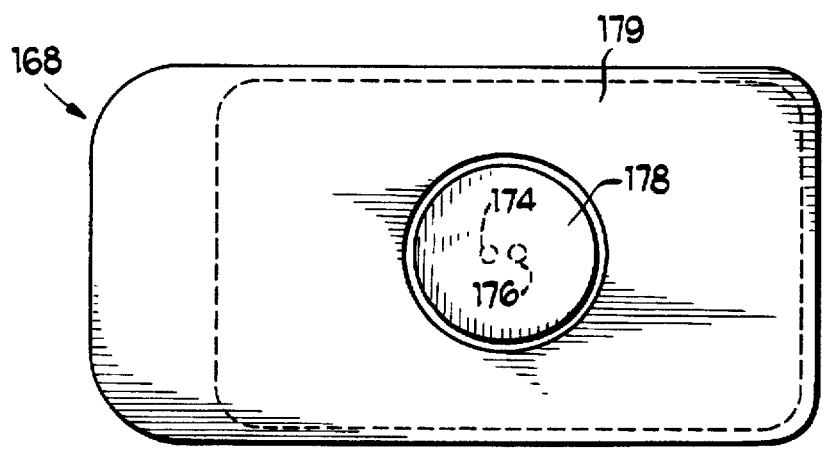
FIG. 7 is a bottom view of the device of FIG. 6.

A device 168 according to FIGS. 6 & 7 is built. The device 168 has two reservoirs 170, 172, one containing a first liquid containing a first compound, and a second containing a second liquid containing a second compound, especially a compound not chemically compatible with the first compound on a long term basis. Alternatively, the second compound can contain a transdermal permeation enhancer. Each compound containing compartment has its own discharge conduit 174, 176 associated therewith. Preferably, the liquids are of the same viscosity. If however the liquids are of varying viscosities, the diameter of each conduit can be adjusted accordingly to achieve similar flow rates from the reservoirs. The depicted device lacks a cannula or needle, and the compounds are admixed on an absorbent pad 178 placed atop the subject's skin for transdermal application.

The reservoirs are contained within a housing 180. The housing 180 also contains a driving battery 182, electronically associated (via resistor 184) with a gas generating cell 186. The gas generating cell 186 is in fluid communication with a "balloon" 188. Upon actuation, a switch 190 completes the electronic circuit between the battery 182 and the gas generating cell 186, causing the cell to generate gas, thus filling the balloon 188. O-rings seal gas inside. As the balloon grows larger, it acts to displace the liquid or fluid contained within the reservoirs 170, 172 which are delivered via the reservoirs' respective conduits 174, 176. An adhesive material 179 may be affixed to an area abutting the outer circumference of the housing 180.

Figure 8:
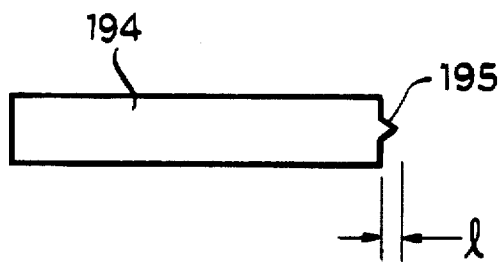
FIG. 8 is an enlarged view of a lancet for use with the invention of FIGS. 6 and 7.

Before the transdermal device is adhered to the subject's skin, a lancet 194 (FIG. 8) having a point 195 of a length to pierce the stratum corneum, but not the epidermis, or other means (e.g. tape, multi-pronged member, or sand paper) is used to destabilize the stratum corneum under the area of the skin where the transdermal pad 178 is to be applied.

Example IV

Figure 9:
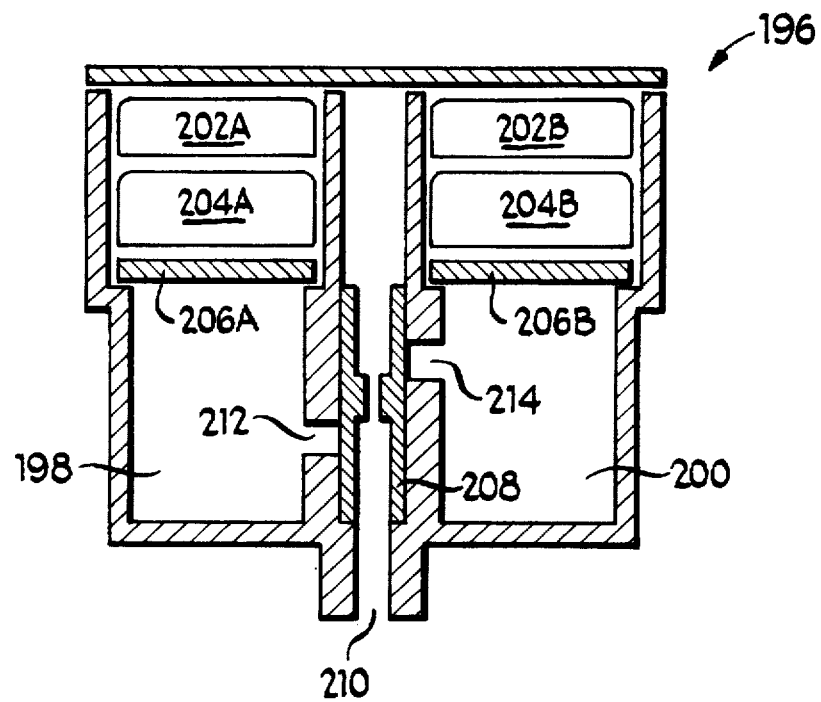
FIG. 9 is an enlarged cross-sectional view of valving useful in delivering two different fluids from an apparatus according to the invention.

An embodiment 196 such as that depicted in FIG. 9 is built. This device 196 has a first fluid chamber 198 and a second fluid chamber 200. The device 196 has batteries 202A, 202B, gas generating cells 204A, 204B, a deformable membrane or bellows 206A, 206B, and a valve 208 made of an elastomeric material. This device 196 may be used to deliver two fluids at different rates through a single outlet 210, and thus has added utility when the combination of the two fluids has a more limited shelf-life than the fluids stored separately. The outlet 210 may be connected to a needle or a sponge (not shown) depending on the delivery required.

Upon actuation, the gas generating cells 204A, 204B begin generating gas which moves the bellows 206A, 206B compressing the fluid chambers 198, 200. Fluid contained within the chambers 198, 200 is forced out ports 212, 214 associated with the chambers and outlets on the valve 208. The check valve is cylindrical and is made of elastic material. The outside diameter is slightly larger than the hole into which it fits. The thin sections on the top and bottom allow the elastomeric material to deform by the pressure in the fluid chambers allowing the fluid to pass by the valve. The thick section in the center will not deflect, preventing fluid from one chamber from entering into the other chamber. Normally, the valve is closed. Valve flexibility, port size (in conjunction with chamber size), current flow, and gas generation speed may all be used, singly or in combination to alter the flow of fluid from the reservoirs.

Example V

Figure 10:
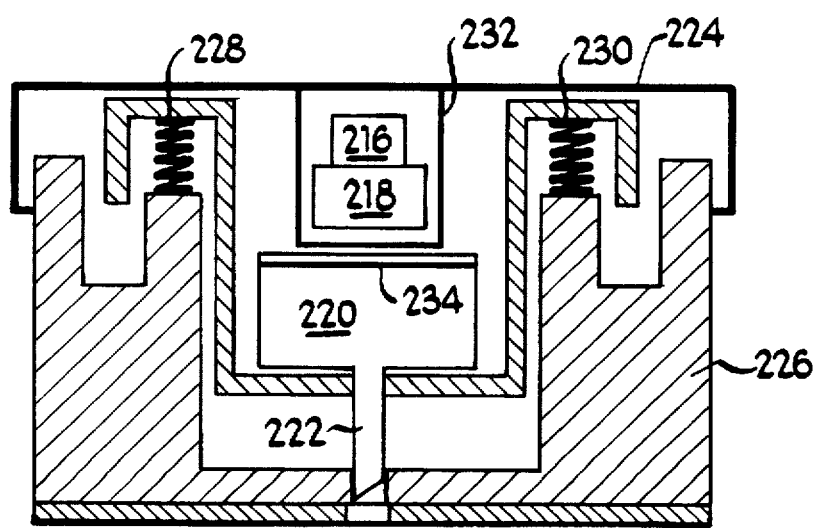
FIG. 10 is an enlarged cross-sectional view of an embodiment of the invention having a needle protrusion and retraction mechanism.

A device is built as depicted in FIG. 10. This device includes a battery 216 in association with a gas generating cell 218. Underneath the cells 216, 218 is a fluid containing reservoir 220. Associated with the fluid containing reservoir 220 is a needle 222. The needle is of such a length that it pierces the skin of a subject (e.g. to a subcutaneous level) when frame 224 is pressed downward by a user, and the needle protrudes from the housing 226 (not shown). Springs 228, 230 act to separate the frame 224 from the housing 226, opening the electrical circuit.

The reservoir 220 is associated in fluid tight communication with the chamber containing the cells 216, 218 via flexible membrane 234. Upon actuation (e.g. by pressing down the frame with respect to the housing), the electrical circuit is completed, and the cells 216, 218 begin generating a driving gas which deforms the membrane 234, thus driving fluid out of the reservoir 220, through the needle 222 and delivering the fluid to the patient.

Although the device is shown as only being actuated when the frame is held down, in alternative embodiments, it can be made as a retractable ball point pen mechanism (e.g. semi-permanent) or as a permanently protruding mechanism (not shown).

Example VI

Figure 11:
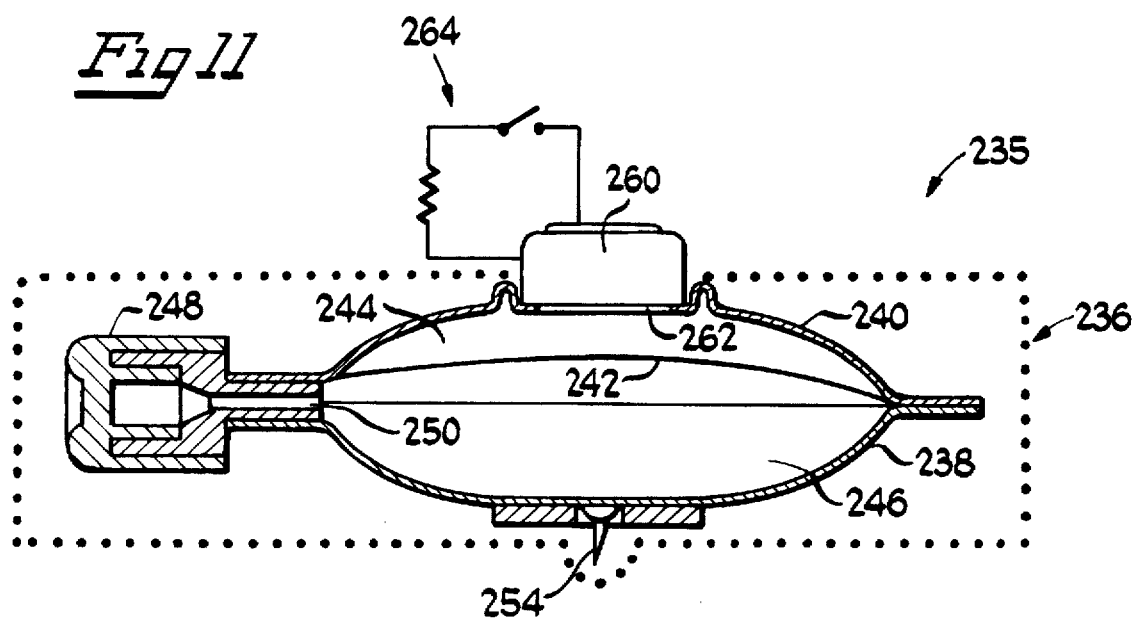
FIG. 11 is an enlarged section view of an embodiment of the invention.
Figure 12:
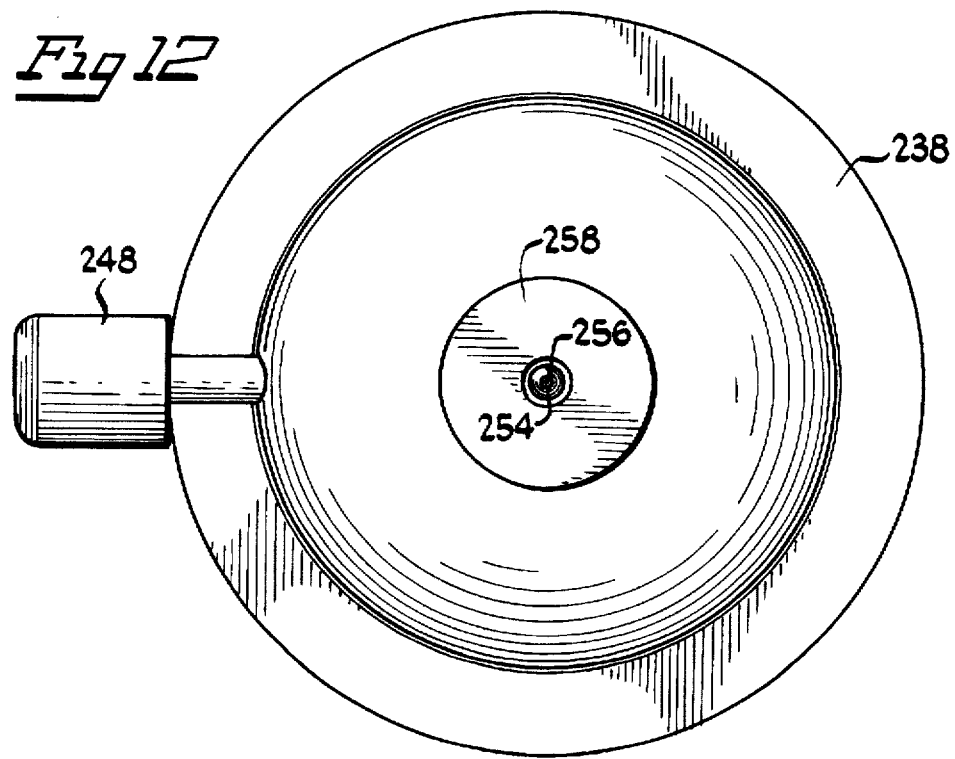
FIG. 12 is an'enlarged bottom view of the embodiment of the preceding figure.

A device 235 as depicted in FIGS. 11 and 12 (shown twice its actual size) is made. In general, the device 235 has two components, a drug package portion 236 (surrounded by a dotted line) and the remainder of the device which comprises an associated control unit for the drug package. In the depicted embodiment, the drug package 236 is integrally formed with the control unit so that the control unit may be disposable. In an alternative embodiment (not shown), the drug chamber is detachably associated with the remainder of the control unit, so that the control unit may be re-used.

The drug package includes two "clamshell" halves 238, 240 joined together (e.g. by a suitable adhesive) between which is pinched a flexible, gas impermeable membrane 242. The membrane 242 separates a driving gas chamber 244 from a chamber 246 for containing a liquid to be delivered. The dispensing liquid chamber 246 is in fluid communication with a septum 248 for receiving the liquid to be delivered. The septum 248 is connected to a conduit 250 which extends into the dispensing liquid chamber 246 for receiving a needle from a needle-bearing syringe filled with dispensing liquid (not shown). The septum 248 acts as a barrier between the conduit 250 and the atmosphere. The dispensing liquid chamber 246 is also associated with a dispensing needle 254.

The interior 256 of the dispensing needle 254 is in fluid communication with the dispensing liquid chamber 246 so that the liquid may be delivered from the device through the lumen 256 of the needle 254.

An adhesive layer 258 adhered to the lower clamshell half 238 surrounds the needle (FIG. 11) for removably attaching the device 235 to the subject's skin.

The upper clamshell half 240 is formed of flexible material so that the device 235 may be "primed" by pushing in on that clamshell half 240 thus driving dispensing liquid into the dispensing needle 254. Alternatively, a mechanical screw or other device can be used to apply pressure to the outside of the packet (turned upside down) until all gas is expelled from the chamber containing the liquid to be delivered. Associated with the upper clamshell half 240 is a galvanic-type gas generating cell 260 in such a manner (e.g. via aperture 262) that exhaust gas from the cell 260 enters the driving gas chamber 244 thus pressurizing it. The galvanic cell is electronically associated with a control circuit 264.

The device 235 works essentially like the other devices described herein. A switch actuates the electronic control circuit 264, starting gas generation from the cell 260, which exhausts into the driving gas chamber 244, thus deforming the membrane 242 which separates the two chambers 244, 246 compressing the liquid containing chamber 246 forcing liquid out of the needle 254. The delivery rate from the delivery needle 254 is relatively slow (e.g. from about 0.1 to about 2.0 cc per hour) and the volume of the chamber 246 containing the liquid to be delivered is greater than 0.5 cc (e.g. from 5 to 200 cc).

Example VII

A device 266 is built as depicted in FIGS. 13 and 14. The device is similar to that of the preceding EXAMPLE.

however instead of using a dispensing needle to deliver the liquid, the device 266 uses a transdermal patch 268 comprised of a small piece of sponge foam. A port 270 extends between the liquid chamber 246 and the sponge foam 268.

Although the invention has been described with regard to certain preferred embodiments, the scope of the invention is to be defined by the claims. For example, besides being useful in medical applications, the device for controlled fluid delivery may be used in dispensing fragrances, insecticides, lubricants, or anti-corrosive agents.

What is claimed is:

1. An apparatus for delivering a fluid, said apparatus comprising:

a housing;

a displaceable membrane disposed within said housing, dividing a portion of said housing into a first chamber and a second chamber, said first chamber formed in part, of said housing, said first chamber for containing fluid for delivery and having a port in fluid communication with said first chamber, and said second chamber for containing a driving gas, said displaceable membrane being impermeable to the driving gas;

a pump for pressurizing driving gas in said second chamber, thereby exerting a force on said displaceable membrane, thus expelling fluid contained within said first member from said port, said pump comprising an electrochemical gas generation cell; and means for delivering fluid from said port to a desired location.

2. The apparatus of claim 1, further comprising a pump activation mechanism.

3. The apparatus of claim 1, further comprising a pump control mechanism.

4. The apparatus of claim 1, further comprising a flow control mechanism for controlling the delivery of the fluid from the apparatus.

5. The apparatus of claim 4, wherein said flow control mechanism comprises electrical circuitry controlling said pump.

6. The apparatus of claim 1, wherein said means for delivering fluid is a needle, and the apparatus further comprises a needle extension mechanism such that, upon activation, the needle extends out of said housing.

7. The apparatus of claim 6, wherein the apparatus further comprises a needle retraction mechanism such that upon termination the needle is retractable within said housing.

8. The apparatus of claim 1, wherein said means for delivering a fluid is a needle, and the apparatus further comprises a needle activation mechanism and a pump activation mechanism such that activation of both mechanisms occurs simultaneously.

9. The apparatus of claim 1, further comprising an adhesive layer disposed on the surface of said housing.

10. The apparatus of claim 9, wherein the adhesive layer contains a pharmaceutically active agent, said pharmaceutically active agent selected from the group of local anesthetics, antiseptics, and mixtures thereof.

11. The apparatus of claim 1, wherein said means for delivering a fluid is a needle, and the apparatus further comprises a needle depth adjustment mechanism for adjusting the length the needle extends from the housing.

12. The apparatus of claim 3, wherein said pump control mechanism comprises electrical circuitry to adjust the voltage to the pump such that the flow of the driving gas is controlled and thus the flow of the fluid is controlled.

13. The apparatus of claim 12, further comprising a timer such that the flow of said delivery fluid and the flow of the first bladder contents can be timed.

14. The apparatus of claim 1, wherein the housing comprises a substantially inexpandable outer shell.

15. The apparatus of claim 1, wherein the housing comprises a generally annular outer shell with the pump and means for delivering fluid disposed generally in the center of the housing.

16. The apparatus of claim 1, wherein said pump comprises an oxygen pump for transferring atmospheric oxygen into said housing and said driving gas comprises oxygen.

17. The apparatus of claim 1, wherein said pump comprises an electrolytic cell comprising a pair of electrodes suspended in an electrolyte and a voltage source such that when voltage is applied to the pair of electrodes, a gas is formed in the electrolyte which exerts a force that expels the liquid.

18. The apparatus of claim 1, wherein said pump comprises a Galvanic cell.

19. The apparatus of claim 1 further comprising a second bladder having an interior, an exterior, and a port extending between said interior and exterior, said second bladder disposed within said housing proximal said first bladder and formed to contain a second fluid within the bladder's interior, wherein said pump pressurizes a driving gas in contact with the second bladder's exterior, said driving gas thereby exerting a force on the exterior of said first bladder, deforming said exterior, and expelling fluid from the first bladder's interior through said port delivering fluid from the first bladder's port to the desired location.

20. The apparatus of claim 1 further comprising a pressure relief valve associated with said second chamber.

21. The apparatus of claim 20 further comprising an inlet port in fluid communication with said first chamber.

* * * * *